US012806411B2

(12) United States Patent
Kryzanski

(10) Patent No.: US 12,806,411 B2
(45) Date of Patent: Nov. 24, 2026

(54) SUBDURAL SOUND SYSTEM WITH A RECEIVING LUMEN FOR PLACING ELECTRODES

(71) Applicant: Hemisphere Medical LLC, Chestnut Hill, MA (US)

(72) Inventor: James Kryzanski, Chestnut Hill, MA (US)

(73) Assignee: Hemisphere Medical LLC, Chestnut Hill, MA (US)

( * ) Notice: Subject to any disclaimer, the term of this patent is extended or adjusted under 35 U.S.C. 154(b) by 160 days.

(21) Appl. No.: 18/606,097

(22) Filed: Mar. 15, 2024

(65) Prior Publication Data

US 2024/0307677 A1 Sep. 19, 2024

Related U.S. Application Data

(60) Provisional application No. 63/452,330, filed on Mar. 15, 2023.

(51) Int. Cl.
*A61N 1/05* (2006.01)
*A61B 17/34* (2006.01)

(52) U.S. Cl.
CPC ........ *A61N 1/0531* (2013.01); *A61B 17/3468* (2013.01); *A61B 2217/007* (2013.01)

(58) Field of Classification Search
CPC .............. A61N 1/0531; A61B 17/3468; A61B 2217/007
See application file for complete search history.

(56) References Cited

U.S. PATENT DOCUMENTS

| | | | | |
|---|---|---|---|---|
| 5,255,691 | A | 10/1993 | Otten | |
| 5,792,110 | A | 8/1998 | Cunningham | |
| 6,304,785 | B1 | 10/2001 | McCreery et al. | |
| 7,022,109 | B1 * | 4/2006 | Ditto | A61B 17/3401 604/164.01 |
| 2003/0009207 | A1 | 1/2003 | Paspa et al. | |
| 2016/0008007 | A1 | 1/2016 | Taha | |
| 2018/0126152 | A1 | 5/2018 | Leven et al. | |
| 2019/0308008 | A1 | 10/2019 | Kryzanski | |
| 2023/0077799 | A1 * | 3/2023 | Kryzanski | A61N 1/0531 607/2 |

FOREIGN PATENT DOCUMENTS

WO WO-2014016765 A2 * 1/2014 ........... A61B 5/0536

OTHER PUBLICATIONS

International Search Report and Written Opinion, PCT Application No. PCT/US2024/020077, mailed Jul. 31, 2024 (19 pages).

* cited by examiner

*Primary Examiner* — Ashley L Fishback
(74) *Attorney, Agent, or Firm* — Faustino Lichauco; Leber IP Law

(57) ABSTRACT

A hypotube sound that comprises a body, a curved tip, a stylet, and an electrode. The body is configured to be placed within a subdural space of a patient and has a curved tip at its leading end. This tip is configured for angled insertion into the subdural space to advance the body to a target site in the subdural space. The stylet, which fits into the channel, is configured to advance to the distal opening and to seal the distal opening after having been inserted into the channel. The is configured to be advanced through the distal opening for placement in contact with dura tissue after having been inserted into the channel.

9 Claims, 7 Drawing Sheets

SUBDURAL SOUND SYSTEM WITH A RECEIVING LUMEN FOR PLACING ELECTRODES

CROSS REFERENCE TO RELATED APPLICATIONS

This application claims priority to U.S. Application No. 63/452,330, filed Mar. 15, 2023, the contents of which is hereby incorporated by reference in its entirety.

BACKGROUND

A seizure is known to have its onset at a particular zone of the cortex called the "ictal zone." In an effort to locate the ictal zone, it is known to place electrodes at various locations on the cortex. Doing so covers a large area of the cortex with electrodes and thus maximizes the chance of finding the ictal zone.

A fibrous covering, known as the "dura," lies over the brain's surface. Between the brain's surface and this dura, it is possible to form a "subdural space." It is within this subdural space that a surgeon would place this array of electrodes.

One method of placing the electrodes is to remove a large piece of a patient's skull and to then carefully lay a grid of electrodes on the brain's surface. Not surprisingly, this highly invasive procedure is rife with risk.

An alternative method, referred to as "stereo-EEG," avoids removal of a large piece of the skull. In this method, the surgeon drills numerous holes in the skull and places electrodes through each hole. This results in electrodes within the brain itself rather than on its surface.

However, this method is also quite invasive since it requires drilling a great many holes. Moreover, it comes with a significant disadvantage: the electrodes will not be on the surface of the brain where the ictal zone is known to be.

U.S. Patent Publ. 2023/0077799, the contents of which are incorporated herein by reference, discloses a way to insert electrodes on the brain's surface without having to remove a large piece of the skull. Instead, one uses a subdural sound assembly to facilitate placement of displaceable subdural electrodes through a small hole that has been drilled through the skull. The electrodes are on long flat strips with multiple electrical contacts. The strips extend through the subdural space along a direction tangential to the brain's surface. The sound is first inserted so that its leading edge is located near the location at which a subdural electrode is to be deployed. The electrodes are then guided through a receiving channel in the sound, after which the sound is retracted, thus leaving the electrodes in the correct locations.

SUMMARY

The invention features a subdural sound system having a hypotube sound. Such a sound has a curved tip and a flexibility that varies along the length of the sound, i.e., a "flexibility gradient." The flexibility gradient is selected such that those portions of the hypotube sound's body that are closer to the sound's leading end are more flexible than those portions that are closer to its trailing end.

The hypotube sound includes an internal lumen, also referred to as a "receiving channel." This lumen extends from a proximal opening, also referred to as the "trailing-end opening," to a distal opening, i.e., the "leading-end opening," which is at the end of the curved tip.

The sound has an elongated body that defines a receiving channel. Prior to the sound's deployment, the receiving channel receives a stylet.

The stylet fits into the receiving channel so that it can be advanced towards the sound's distal opening. In some embodiments, the stylet is structured to substantially seal the sound's distal opening. This reduces the risk of injury to brain tissue as the sound advances through the subdural space. Such injury can occur as a result of tissue being accidentally collected by the distal opening.

The stylet also serves additional functions. In some embodiments, the stylet is configured to provide an alternative steering mechanism to assist the surgeon in guiding the sound to the correct location. In other embodiments, the stylet comprises an irrigation channel that delivers irrigation fluid from a fluid reservoir. In such embodiments, an adaptor connects the fluid reservoir to the irrigation channel. An example of a suitable adapter is one that relies on a Luer lock.

Once the subdural sound has been guided to its destination, the stylet is retracted through the sound's proximal opening. The now vacated receiving channel is then used to advance an electrode. The sound thus acts as a sheath to prevent the electrode from accidentally piercing or otherwise adversely interacting with the brain tissue. Examples of suitable electrodes include a thin cylindrical electrode with multiple ring-shaped electrical contacts, a depth electrode, and a flat-surface electrode with electrical contacts disposed on the flat surface.

The foregoing process can be repeated by introducing the sound (or a different sound) through the same hole, guiding it towards a different target site within the subdural space, and advancing another electrode towards the distal opening of the sound.

As noted, the hypotube subdural sound is structured to have a flexibility that varies along the length of the sound. This means that, for a given force, the displacement will differ at different points along the length. In addition, this flexibility depends on direction. Thus, the deflection of the sound in response to a force depends on the direction of that force.

In some embodiments, the hypotube sound is constructed from lubricious material.

In other embodiments, the sound's elongated body has a varying flexibility profile. The variable stiffness profile, along with the curved tip extending from the distal end of the sound allows the use of a simple nudging motion to negotiate the initial sharp angle entry needed to place the curved tip into a position to open up a subdural space.

Further embodiments include those in which the sound is fitted with optical, electrical, or chemical sensors that confirm location in the subdural space during the sound's passage therethrough.

Additional optional features include implementations in which the deployed electrodes are used for uses other than epilepsy, including for cortical stimulators, and cyber-prostheses, for example to form a brain-machine interface.

In some embodiments, the electrodes are constituents of a permanent prosthesis. In other embodiments, the electrodes are only for temporary monitoring.

The structural features of the subdural sound described herein allow the subdural sound to advance in the subdural space with minimal resistance and with reduced risk of injuring the brain tissue, for example by accidentally piercing or abrading that tissue. A surgeon can then use gentle pushing and prodding movements to guide sound to its destination without requiring elaborate navigation equipment or an imaging apparatus.

Of course, the availability of such equipment is nevertheless helpful at enabling more accurate guidance. For example, image data may be obtained via an optical fiber included with the subdural sound can be used to assist guidance. Alternatively, the location of the sound can be determined through external imaging, using X-ray imaging or magnetic resonance imaging. For this purpose, it is helpful to fit the sound with radiopaque indicators.

In some embodiments, the subdural sound includes a distance-determination mechanism, embodiments of which include markings. This distance-determination mechanism is useful to see at a glance how much of the sound is already within the patient's body.

Additional advantages of the implementations described herein is subsequent removal of an electrode after it has been inserted is much easier than removing conventional flat subdural electrodes, the removal of which typically requires taking the patient to the operating room for a complicated electrode removal procedure.

In one aspect, the invention features a subdural sound system comprising a hypotube sound, that comprises an elongated body that comprises a trailing end that has a proximal opening, a leading end that has a distal opening, and a channel that extends from the proximal end to the leading end, the channel being a receiving channel and that is configured to be placed within a subdural space of a patient; a curved tip, which is at the leading end, is configured for angled insertion into the subdural space to advance the body to a target site in the subdural space; a stylet that fits into the channel and that is configured to advance to the distal opening and to seal the distal opening after having been inserted into the channel, and an electrode that is configured to be advanced through the distal opening for placement in contact with dura tissue in the subdural space after having been inserted into and through the channel.

In some embodiments, the body comprises a flexible circular lumen that defines the channel.

In other embodiments, the body comprises a first region and a second region that is adjacent to the second region. In such embodiments, the first region has a first rigidity and the second region has a second rigidity that differs from the first rigidity.

Also among the embodiments are those in which the body comprises a first region and a second region that is adjacent to the second region, wherein the second region includes the leading end and the second region is more flexible than the first region.

In still other embodiments, the curved tip comprises first, second, third, and fourth sides. In these embodiments, the first side has a curved profile in relation to a first axis of the body, the second side has a flat profile in relation to the first axis, and the third and fourth sides define a tapering profile in relation to a second axis of the body.

Among the embodiments are those in which stylet comprises an internal lumen that is configured to deliver irrigation fluid that passes through the channel and those that comprise an irrigation adapter that is coupled to a proximal end of the stylet and that is configured to direct irrigation through the channel.

A variety of electrodes are usable. Among these are a cylindrical electrode, a multiple ring electrode with ring contacts extending along a cylindrical body, and an elongated structure with electrical contacts disposed on a flat side thereof.

In another aspect, the invention features a method that comprises forming a hole in a skull of a patient to access target tissue in a subdural space in a brain area of the patient, fitting a stylet into a channel defined in a body of a sound, the channel being a receiving channel that extends from a proximal opening at a trailing end of the sound to a distal opening at a leading end of the sound, the sound being a hypotube sound, the body being an elongated body having a curved tip at the leading end, causing the stylet to seal the distal opening, directing the sound to a target site in the subdural space, upon reaching the target site, removing the stylet from the receiving channel, after having removed the stylet, fitting an electrode into the receiving channel, and advancing the electrode through the channel towards the distal end for placement thereof in contact with target tissue in the subdural space.

These and other features of the invention will be apparent from the following detailed description and the accompanying figures, in which:

DETAILED DESCRIPTION

Figure 1:
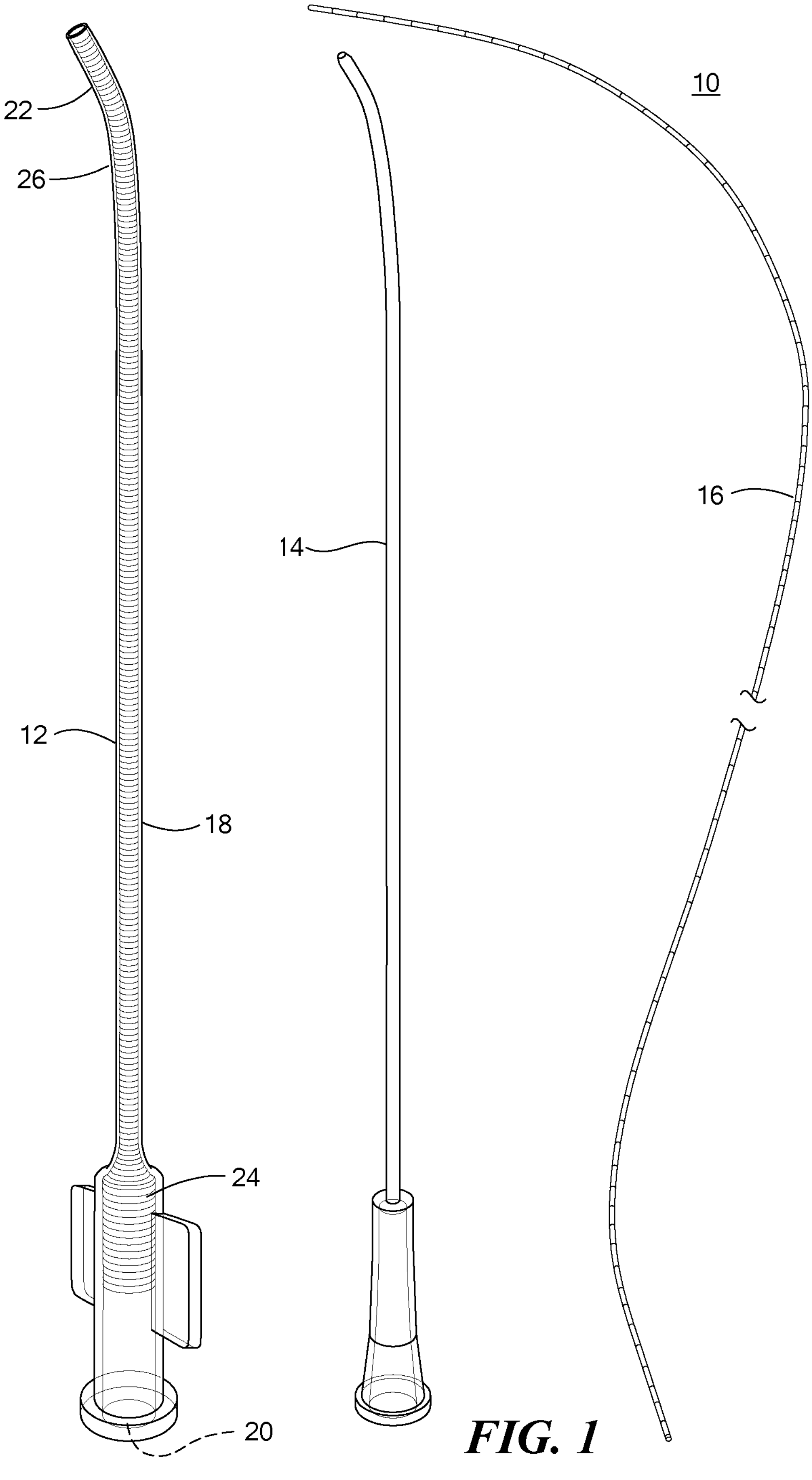
FIG. 1 shows components of a subdural sound system.
Figure 2:
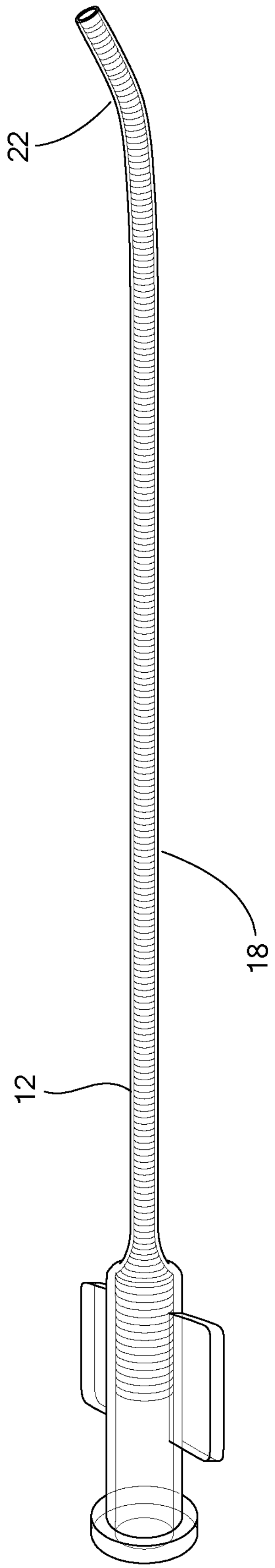
FIGS. 2-4 and 6-7 are close-up views of the hypotube sound from the sound system of FIG. 1.
Figure 3:
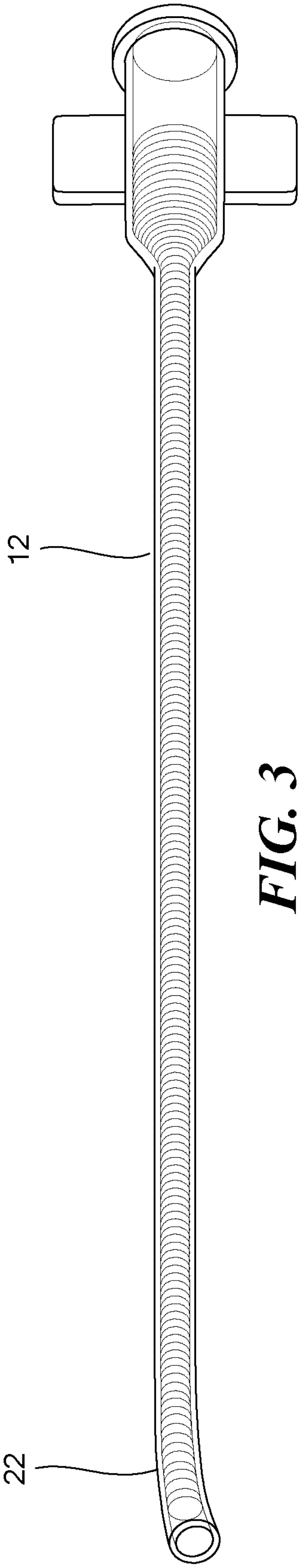
Figure 4:
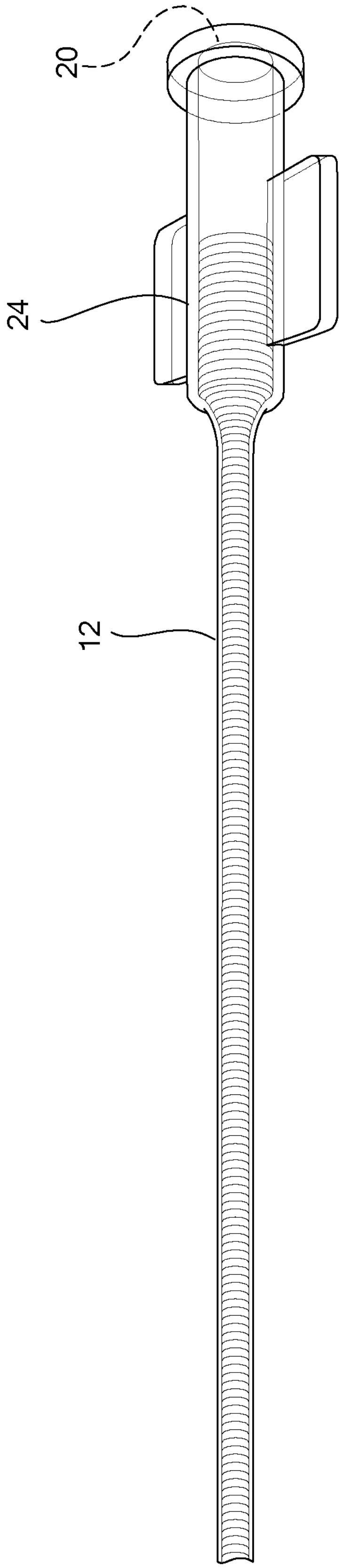

FIG. 1 below shows a subdural sound system 10 that has been disassembled to show components thereof. The components include the hypotube sound 12, the stylet 14 (or "guide"), and an electrode 16 (the right most component of FIG. 1), which in this case is a cylindrical electrode such as a depth electrode.

FIGS. 2-4 and 6-7 are close-up views of the hypotube sound 12.

Figure 5:
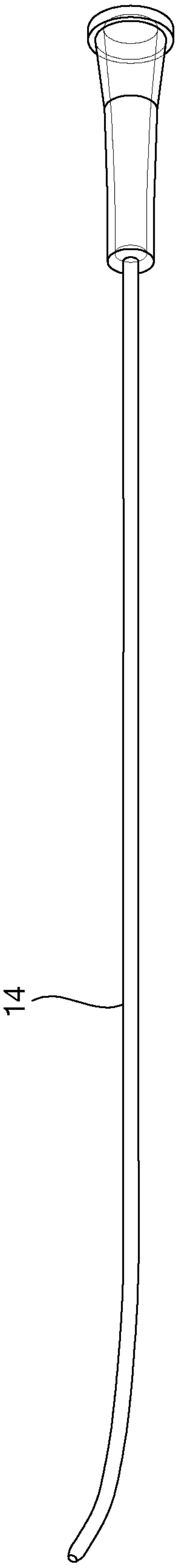
FIG. 5 is a close-up view of a stylet from the sound system of FIG. 1.
Figure 6:
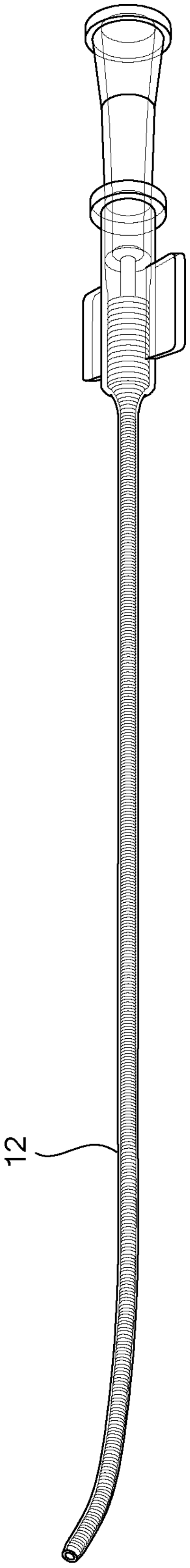
Figure 7:
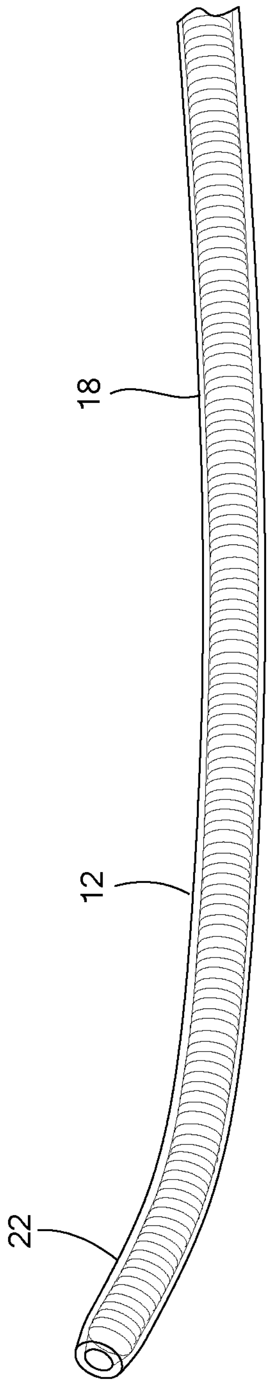
Figure 8:
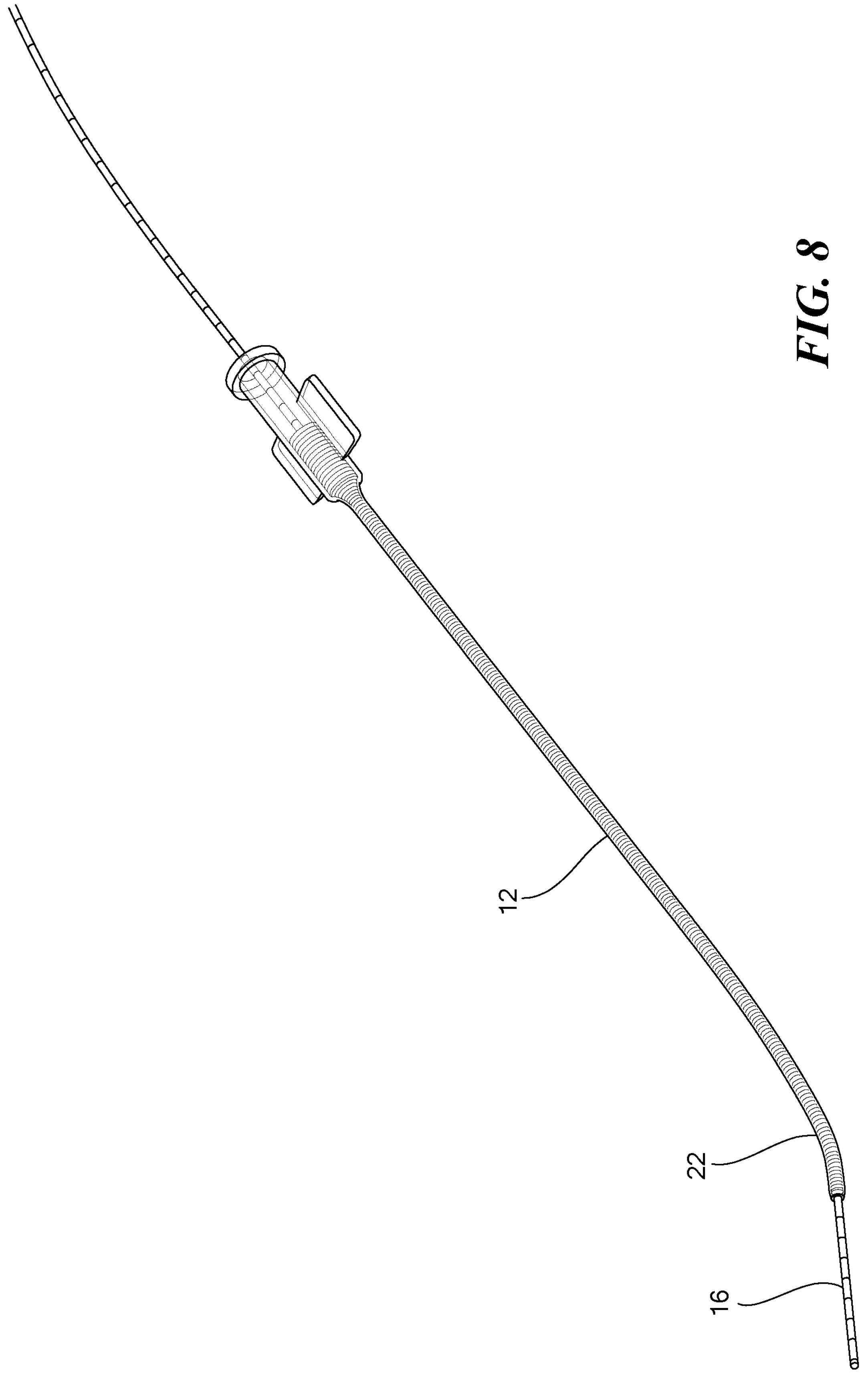
FIGS. 8-10 are views showing a cylindrical electrode of the sound system of FIG. 1 after having been placed through a receiving channel of the hypotube sound of FIGS. 2-4 and 6-7.
Figure 9:
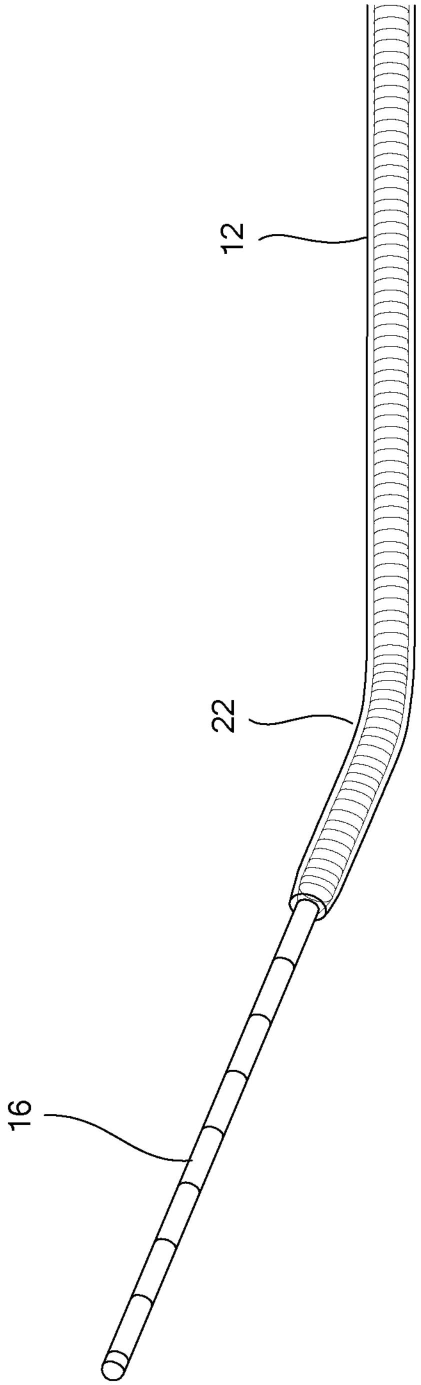
Figure 10:
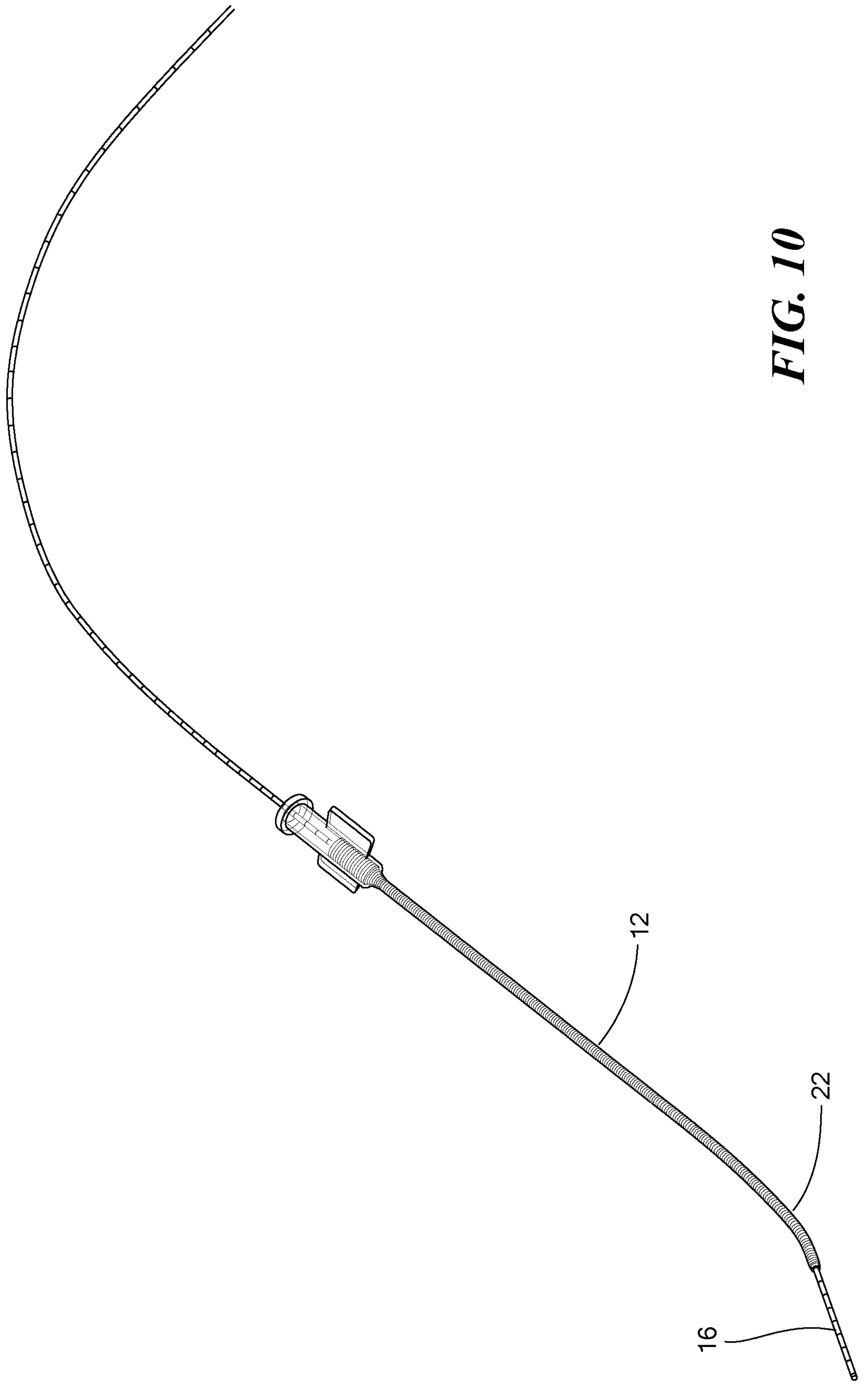

FIG. 5 is a close-up view of a stylet 14, while FIGS. 8-10 are views showing a cylindrical electrode 16 placed through the receiving channel of the hypotube sound 12.

Referring to FIG. 1, the hypotube sound 12 includes an elongated body 18 configured to be placed within a subdural space of a brain area of a patient. The elongated body 18 defines a receiving channel 20 and a curved tip 22. The receiving channel 20 extends from a proximal opening at a trailing end 24 of the hypotube sound 12 to a distal opening at a leading end 26 of the hypotube sound 12. The curved tip 22, which is at the leading end 26 of the elongated body 18, is configured for angled insertion into the subdural space of the patient to advance the elongated body 18 to a target site in the subdural space.

The system 10 further includes a stylet 14 and an electrode 16, both of which are configured to be inserted into the receiving channel 20.

The stylet 14 fits into the receiving channel 20. As a result, the stylet 14 can be inserted into the receiving channel 20 so as to advance to the distal opening and substantially seal the distal opening.

When the receiving channel 20 is no longer occupied by the stylet 14, it is possible to insert the electrode 16 into the receiving channel 20 and to advance it through the distal opening for placement contacting the dura tissue in the subdural space.

Examples of an electrode 16 include a cylindrical electrode, a multiple-ring electrode having ring-shaped contacts disposed on a cylindrical body, and a flat-surface electrode that comprise an elongated structure with electrical contacts disposed on a substantially flat first side thereof.

In some embodiments the elongated body 18 includes a flexible circular lumen defining the receiving channel 20. Also among the embodiments are those in which the elongated body 18 of the hypotube sound 12 includes adjacent regions along a length of the subdural sound. Each of these adjacent regions has a different rigidity. In a preferred embodiments, the most flexible and least rigid portion of the elongated body 18 is its distal portion.

In some examples, the curved tip 22 includes a first side having a curving profile defined in relation to a first axis of the elongated body 18, a second side with a substantially flat profile in relation to the first axis, and third and fourth sides defining a tapering profile in relation to a second axis of the elongated body 18.

In some embodiments, the stylet 14 includes an internal channel configured to deliver irrigation fluid passable through the receiving channel 20 of the hypotube sound 12. The subdural sound system 10 may further include an irrigation adapter coupled to a proximal end of the stylet 14, the irrigation adapter being connectable to an irrigation mechanism, and configured to direct irrigation fluid through the receiving channel 20 defined in the elongated body 18 of the hypotube sound 12 to facilitate displacement of subdural sound through the subdural space.

In operation, deploying electrodes 16 in the subdural space of a patient includes forming a hole in a skull of a patient to access target tissue in a subdural space in a brain area of the patient, and fitting a stylet 14 into a receiving channel 20 defined in an elongated body 18 of a hypotube sound 12, with the receiving channel 20 extending from a proximal opening at a trailing end of the hypotube sound 12 to a distal opening at the leading end of the hypotube sound 12, and with the hypotube sound 12 further including a curved tip 22 at a distal end of the elongated body 18. The fitted stylet 14 substantially seals the distal opening of the elongated body 18 of the hypotube sound 12. The procedure to deploy the electrode 16 further includes directing through the hole the hypotube sound 12 with the stylet 14 fitted in the receiving channel 20 of the hypotube sound 12 to a target site in the subdural space, removing the stylet 14 from the receiving channel 20 of the elongated body 18 of the hypotube sound 12, fitting an electrode 16 (cylindrical or flat-surface) into the receiving channel 20 of the elongated body 18 of the hypotube sound 12 that was occupied by the stylet 14, and advancing the electrode 16 through the receiving channel 20 defined in the elongated body 18 of the hypotube sound 12 towards the distal end of the of the hypotube sound 12 at the target site for placement of the electrode 16 in contact with target tissue in the subdural space of the patient.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of ±20% or ±10%, ±5%, or ±0.1% from the specified value, as such variations are appropriate in the context of the systems, devices, circuits, methods, and other implementations described herein. "Substantially" as used herein when referring to a measurable value such as an amount, a temporal duration, a physical attribute (such as frequency), and the like, also encompasses variations of ±20% or ±10%, ±5%, or ±0.1% from the specified value, as such variations are appropriate in the context of the systems, devices, circuits, methods, and other implementations described herein.

As used herein, including in the claims, "or" as used in a list of items prefaced by "at least one of" or "one or more of" indicates a disjunctive list such that, for example, a list of "at least one of A, B, or C" means A or B or C or AB or AC or BC or ABC (i.e., A and B and C), or combinations with more than one feature (e.g., AA, AAB, ABBC, etc.). Also, as used herein, unless otherwise stated, a statement that a function or operation is "based on" an item or condition means that the function or operation is based on the stated item or condition and may be based on one or more items and/or conditions in addition to the stated item or condition.

Although particular embodiments have been disclosed herein in detail, this has been done by way of example for purposes of illustration only and is not intended to be limiting with respect to the scope of the appended claims, which follow. Features of the disclosed embodiments can be combined, rearranged, etc., within the scope of the invention to produce more embodiments. Some other aspects, advantages, and modifications are considered to be within the scope of the claims provided below. The claims presented are representative of at least some of the embodiments and features disclosed herein. Other unclaimed embodiments and features are also contemplated.

Having described the invention and a preferred embodiment thereof, what is claimed as new and secured by letters patent is:

What is claimed is:

1. A method comprising: forming a hole in a skull of a patient to access target tissue in a subdural space in a brain area of said patient, fitting a stylet into a channel defined in a body of a sound, said channel being a receiving channel that extends from a proximal opening at a trailing end of said sound to a distal opening at a leading end of said sound, said sound being a hypotube sound, said body being an elongated body having a curved tip at said leading end, causing said stylet to seal said distal opening, directing said sound to a target site in said subdural space, upon reaching said target site, removing the stylet from said receiving channel, after having removed said stylet, fitting an electrode into said receiving channel, and advancing said electrode through said channel towards said distal end for placement thereof in contact with target tissue in said subdural space, said method further comprising introducing a different sound through said hole and guiding said different sound to a different target site, wherein said different target site differs from said target site.

2. The method of claim 1, further comprising visually inspecting markings on said sound and determining an extent to which said sound has entered said patient's body based at least in part on having visually inspected said markings.

3. The method of claim 1, wherein directing said sound to said target site comprises forming said subdural space.

4. The method of claim 1, further comprising selecting said patient to be an epileptic patient.

5. A method comprising: forming a hole in a skull of a patient to access target tissue in a subdural space in a brain area of said patient, fitting a stylet into a channel defined in a body of a sound, said channel being a receiving channel that extends from a proximal opening at a trailing end of said sound to a distal opening at a leading end of said sound, said sound being a hypotube sound, said body being an elongated body having a curved tip at said leading end, causing said stylet to seal said distal opening, directing said sound to a target site in said subdural space, upon reaching said target site, removing the stylet from said receiving channel, after having removed said stylet, fitting an electrode into said receiving channel, and advancing said electrode through said channel towards said distal end for placement thereof in contact with target tissue in said subdural space, said method further comprising using a nudging motion to negotiate an initial entry at an angle to place said curved tip into a position to open up said subdural space.

6. The method of claim 5, further comprising visually inspecting markings on said sound and determining an extent to which said sound has entered said patient's body based at least in part on having visually inspected said markings.

7. The method of claim 5, wherein directing said sound to said target site comprises forming said subdural space.

8. The method of claim 5, further comprising selecting said patient to be an epileptic patient.

9. The method of claim 5, further comprising introducing a different sound through said hole and guiding said different sound to a different target site, wherein said different target site differs from said target site.

* * * * *